(12) United States Patent
Hill

(10) Patent No.: US 6,563,012 B2
(45) Date of Patent: May 13, 2003

(54) SKIN EXFOLIATION APPARATUS AND METHOD

(76) Inventor: John M Hill, 707 Ixora Ave., Ellenton, FL (US) 34222

(*) Notice: Subject to any disclaimer, the term of this patent is extended or adjusted under 35 U.S.C. 154(b) by 0 days.

(21) Appl. No.: 09/865,252

(22) Filed: May 25, 2001

(65) Prior Publication Data

US 2001/0023327 A1 Sep. 20, 2001

Related U.S. Application Data

(63) Continuation-in-part of application No. 09/407,585, filed on Sep. 28, 1999.

(51) Int. Cl.$^7$ ............................................. A61F 13/00
(52) U.S. Cl. .............................. 602/41; 602/42; 602/43; 602/44; 602/45; 602/46
(58) Field of Search ............................... 602/41–47, 52, 602/903; 434/401, 443; 514/844, 846

(56) References Cited

U.S. PATENT DOCUMENTS

| | | | |
|---|---|---|---|
| 4,447,482 A | * | 5/1984 | Heinzelman et al. ...... 428/42.3 |
| 4,699,930 A | * | 10/1987 | Suga ........................... 514/25 |
| 4,752,472 A | * | 6/1988 | Kligman |
| 5,043,356 A | * | 8/1991 | Fulton, Jr. ................... 514/549 |
| 5,316,838 A | * | 5/1994 | Crandall et al. |
| 5,720,963 A | * | 2/1998 | Smith |
| 5,810,756 A | * | 9/1998 | Montecalvo et al. |

FOREIGN PATENT DOCUMENTS

WO            99/26572        *   6/1999

* cited by examiner

*Primary Examiner*—Nicholas D. Lucchesi
*Assistant Examiner*—Lalita M Hamilton
(74) *Attorney, Agent, or Firm*—David Kiewit

(57) ABSTRACT

An immediate and visible temporary cosmetic improvement in skin condition is obtained by a multi-stage exfoliation method having one of several visible end points. Preferred methods involve repeatedly attaching specularly reflective exfoliation sheets having a pressure sensitive adhesive to a selected part of the user's body and then removing each sheet by grasping one edge and pulling it along the user's body. After each repetition the user inspects either the sheet that has just been removed, or a blemished area of the body to monitor the amount of exfoliated tissue. When the amount of tissue on a sheet is discernibly less than that removed in the immediately previous repetition, when a pattern of tissue on a sheet matches a pattern on a comparison strip, or when the blemish has been substantially reduced in size, the process is completed.

16 Claims, 3 Drawing Sheets

SKIN EXFOLIATION APPARATUS AND METHOD

CROSS REFERENCE TO RELATED APPLICATIONS

This application is a continuation in part of allowed U.S. application Ser. No. 09/407,585, filed Sep. 28, 1999.

BACKGROUND OF THE INVENTION

1. Field of the Invention

The invention relates to cosmetic treatments for temporarily improving the surface texture of human skin. More specifically, the invention relates to treatments involving the removal of, or that promote the removal of, outer layers of the epidermis.

2. Background Information

Many approaches have been proposed and used for removing blemishes from and for improving the surface texture of the face and other portions of the human body by removing an outer portion of the epidermis. Known approaches include those of a surgical or quasi-surgical nature and include dermabrasion and laser surgery. Approaches of particular interest to the present invention are adhesive exfoliation methods in which an outer portion of the skin is peeled off after being adhered to some substance or another. In some of these approaches (commonly called "face masks" or "beauty masks") a liquid or viscous adherent material is applied to the portion of the body to be exfoliated and is allowed to dry or set up. When the dried or solidified material is peeled off the body some dead surface tissue is removed from the skin. Another adhesive exfoliation technique is generally known as "tape stripping" and involves adhering a tape having a pressure-sensitive adhesive backing to the user's body and then pulling the tape off the body part to remove an outer layer of skin.

Some of the more popular approaches to exfoliation are primarily chemical in nature and involve application of an exfoliant material that attacks the outer layers of the skin. These chemical approaches include, inter alia, retin-A, glycolic acid and alpha hydroxy acid "peels". A notable variation on this theme is the use of pre-cut segments of an adhesive coated tape in which an exfoliant material has been incorporated into the adhesive. These products, which include the Sudden-Change(Hydroxy-Patch distributed in the US by CCA Industries, Inc. of East Rutherford N.J., use a generally weak adhesive to hold the active chemical ingredients in contact with a user's skin for the duration of a treatment period, which may extend over the greater part of an hour.

Of particular note is U.S. Pat. No. 5,720,963 wherein Smith teaches a variety of long term skin treatments, several of which include a regime of five to ten tape stripping steps repeated twice daily in order to chronically disrupt a skin water barrier. Smith also teaches that more severe treatments can be carried out less frequently (e.g., every second or third day) by using a more aggressive skin-adhering adhesive, such as a cyanoacrylate adhesive. Although he discloses several different tape stripping approaches in U.S. Pat. No. 5,720,963, Smith states that his tape stripping method has numerous drawbacks, which include a wide range of response of various individuals to tape stripping, as well as a stated need for an expensive laboratory instrument to monitor the process. Moreover, Smith's teaching is directed entirely towards treatments extending over several months before obtaining discernible results. He does not teach any methods that result in immediate improvements associated with tape stripping.

In another discussion of tape stripping, which is found in a promotional writing for a line of exfoliation soaps and lotions sold by Clinique Laboratories Inc., a single tape stripping of skin on the back of the consumers hand is proposed as a diagnostic test. This test is preferably carried out using a piece of transparent adhesive tape on which the user can view the removed tissue to solely demonstrate the presence of easily exfoliated dead skin.

BRIEF SUMMARY OF THE INVENTION

One feature of the invention is an immediate and visible improvement in skin condition that is preferably obtained by a multi-stage exfoliation method having one of several different end points and providing a margin of safety whereby the user's skin is not significantly irritated if the user ignores an end point and continues to carry out additional and unnecessary exfoliation steps.

A preferred method of practicing the skin exfoliation method of the invention comprises the steps of: 1) exposing an adhesive coated surface of a portion of a flexible exfoliation sheet that is preferably selected to be comparable in size and shape to a portion of the user's body that is to be exfoliated; 2) adhering the exfoliation sheet to the portion of the user's body; 3) grasping an edge portion of the exfoliation sheet and pulling the exfoliation sheet along the surface of the portion of the body so as to separate it therefrom; 4) visually monitoring the amount of skin exfoliated and blemishes removed or substantially reduced; 5) preparing a new exfoliation sheet and repeating steps 1) through 4) until reaching an end point, which may be one of those described in the following detailed description of the invention. Although an adhesive coated surface may be exposed by peeling a portion of a roll of adhesive film from the roll, the practice of this method is facilitated by die-cutting a composite sheet so as to define the size and shape of the adhesive-covered surface portion that is to be exposed when the exfoliation sheet is separated from whatever backing layer is employed. In one variant on the method, only the backing sheet is die-cut so portions of it may be removed from the exfoliation sheet, leaving an exfoliation sheet that may have alignment indicia printed on it. In another variant, the exfoliation sheet is die-cut so that portions of it can be removed from the uncut backing sheet.

In the method described above, several different end point determinations are within the scope of the invention. One such end point determination comprises comparing sequentially removed sheets until the amount of exfoliated skin noted is discernibly less than the amount of exfoliated skin retained on the respective exfoliation sheet employed in the immediately preceding repetition. A second arrangement calls for comparing each removed exfoliation sheet with a comparison sheet that displays a plurality of visually distinct regions corresponding to various amounts of removed tissue. Yet another approach, that is particularly useful when dealing with blemishes such as enlarged pores, some forms of acne, wrinkles and lines, rough areas, flaking skin, excessive epidermal build-up, age spots, accumulated pigmentation, freckles, etc., comprises repeating the exfoliation step and inspecting the exfoliated portion of the body after each repetition until visually observing, after a last one of the repetitions, that the blemish has been removed or substantially reduced in size.

In a further aspect, the invention provides a skin exfoliation kit that includes enough flexible exfoliation material for several iterated stripping operations on a user's face or other selected portion of his or her body. This kit comprises a supply of exfoliation material that may comprise a plurality of pre-cut, or die-cut pressure sensitive adhesive-coated exfoliation sheets, or may comprise a roll of exfoliation film from which sheets may be cut or otherwise separated as required. In either event, the exfoliation sheets preferably comprise reflective, or partially reflective, surfaces and a generally transparent medical-grade hypo-allergenic adhesive film. Each of the sheets preferably has a size and shape adapted to the predetermined portion of the body. Separating an exfoliation sheet from a backing sheet, peeling a portion of film off a roll in which the backing sheet function had been served by the non-adhesive-coated side of another portion of the roll, or separating one of a stack of pre-cut exfoliation sheets arranged so that the adhesive-coated surface of each sheet was initially covered by the adhesive-free surface of a neighboring sheet, exposes a corresponding portion of pressure sensitive adhesive that had previously been protected. Once one has exposed the working fraction of the adhesive, it can be used for skin exfoliation. In some cases two protective backing sheets are used, with the smaller of two backing sheets disposed over an edge portion of the exfoliation sheet. In these cases, when the smaller backing sheet is removed a handle can be attached adjacent one edge of the sheet. In other cases that portion of the sheet from which the backing layer was not removed can be grasped and used as a handle when pulling the exfoliation sheet off the body.

In yet a further embodiment of the invention, an exfoliation kit may comprise one or more comparison sheet(s) displaying a plurality of regions having gradually varying appearance. The appearance of each of the regions is selected to be respectively representative of a predetermined amount of exfoliated skin, and the regions are preferably arranged so that a region representative of a minimal amount of exfoliated tissue at one end of a row and one representative of a maximal amount of exfoliated tissue at the other end. A user may select one of these regions as a target representative of a desired end point. In subsequent exfoliation operations the user can then compare the amount of exfoliated tissue adhering to each of a series of exfoliation sheets as the each sheet is removed and can terminate the process when the visual appearance of the most recently removed sheet matches that of the target.

Another feature of the invention is the provision of a plurality of sections of pressure sensitive exfoliation sheets that can be viewed sequentially in to allow a user to monitor progress during a skin exfoliation process.

Preferred methods described herein provide a means of detecting an end point to avoid irritation of the skin while obtaining the best cosmetic results in an iterative exfoliation process, and do so without any need for expensive laboratory apparatus for monitoring.

Although it is believed that the foregoing recital of features and advantages may be of use to one who is skilled in the art and who wishes to learn how to practice the invention, it will be recognized that the foregoing recital is not intended to list all of the features and advantages, Moreover, it may be noted that various embodiments of the invention may provide various combinations of the hereinbefore recited features and advantages of the invention, and that less than all of the recited features and advantages may be provided by some embodiments.

DETAILED DESCRIPTION OF THE INVENTION

Figure 1:
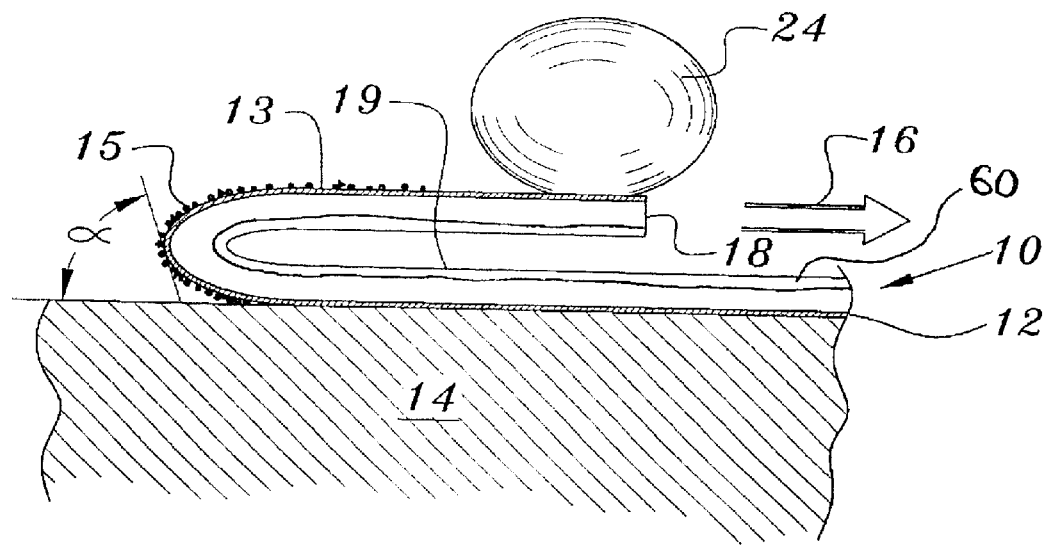
FIG. 1 is a partly elevational view depicting a stage in a skin exfoliation process.
Figure 2:
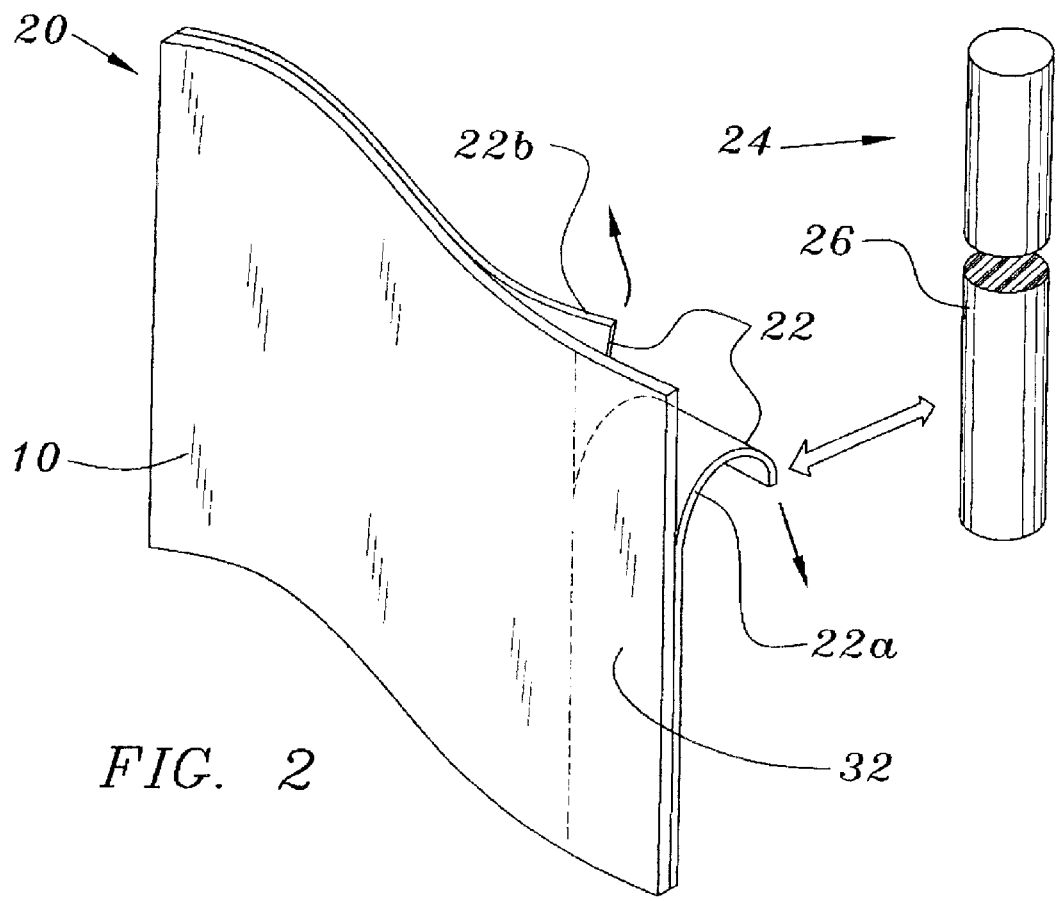
FIG. 2 is a partly exploded view of a pre-cut exfoliation sheet with a protective backing sheet and an attachable handle.
Figure 3:
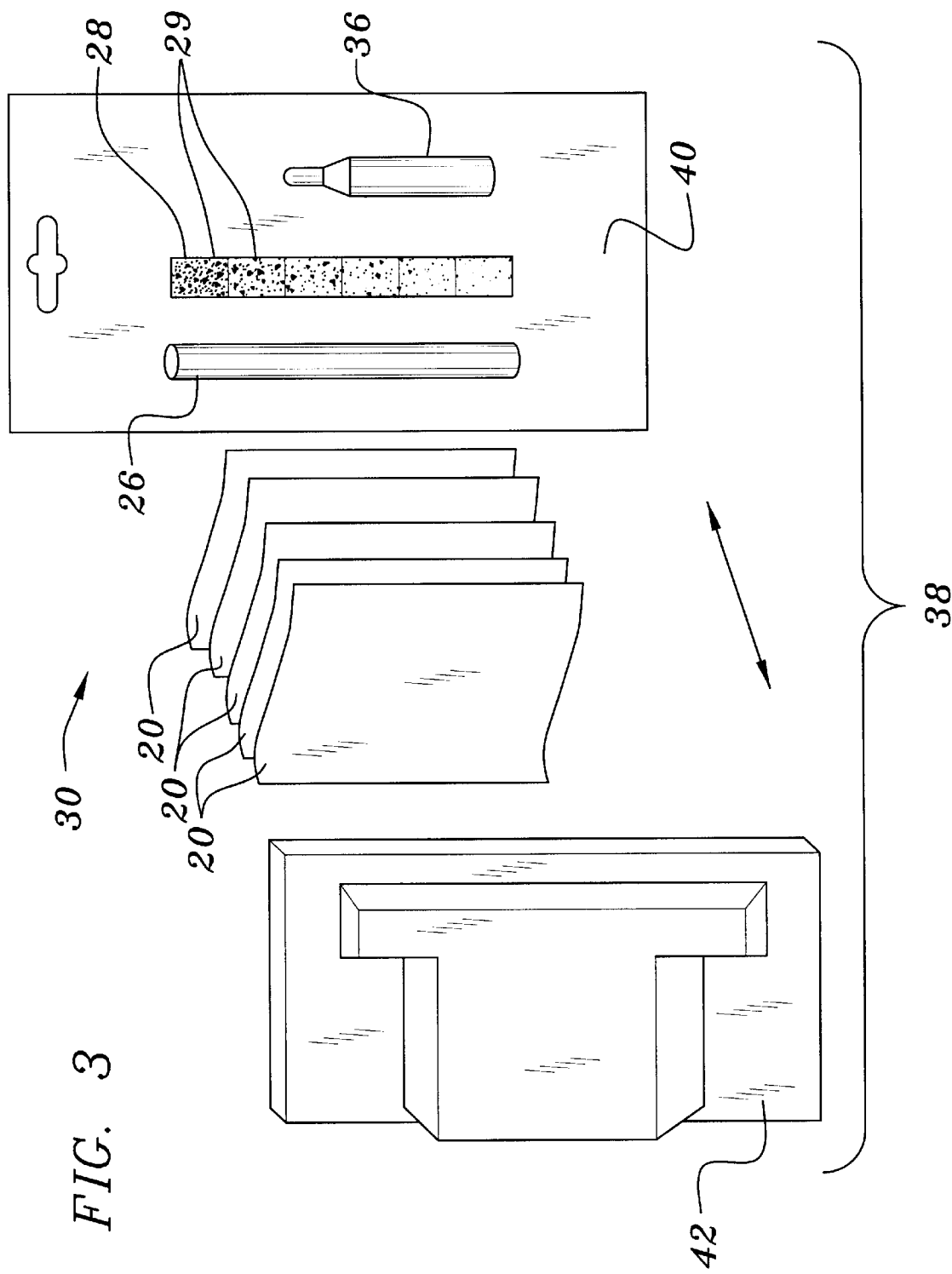
FIG. 3 is an exploded view of an exfoliation kit of the invention.

An adhesive exfoliation process, as discussed above, may comprise the use of a flexible exfoliation film 10 having a layer of a pressure-sensitive adhesive 12 disposed on one side 13 thereof. As is well known, this adhesive may be used to adhere a portion of the film 10 to a predetermined portion of a user's body 14 so that when the film 10 is removed (e.g., by pulling the sheet back along itself from one edge, as is depicted in FIG. 1 with the twin-tailed arrow 16), a strippable portion of the user's epidermis 15 adheres to the adhesive film and is thereby lifted away from the user's body 14.

A method of exfoliation that is used for removal of blemishes is iterative in nature and calls for the use of a plurality of portions of an exfoliation film 10, with a new sheet of the film 10 being used in each iteration. This plurality of portions of film 10 may comprise a plurality of pre-cut sheets 20, each of which may have one or more backing sheets 22 initially disposed on its adhesive-coated side 13. After a first sheet is pulled away from the predetermined portion of a user's body, the user practicing the preferred method visually examines the portion of his or her body that is being exfoliated to see if the blemish has been removed or substantially reduced in size. If not, the process is repeated.

In several preferred methods of the invention, adhesive-coated exfoliation sheets 10 are used and after each consecutive exfoliation of a predetermined area the user visually inspects the sheet 10 to assess the amount of exfoliated tissue adhering to that sheet. Initial embodiments of the invention used a highly transparent adhesive film having a smooth, glossy surface. This film was inspected in bright transmitted light. A presently preferred approach uses a reflective film having transparent adhesive coating on one or both side(s) so that the inspection can be made using bright specularly reflected light which illuminates and defines more of the translucent exfoliated tissue. In either case, a second sheet is then employed in the same fashion as the first, and the amount of tissue lifted away with the second sheet is compared with that lifted with the first sheet. These steps of applying an exfoliating sheet 10, pulling it away from the body, and determining the amount of tissue exfoliated are repeated until the user observes that the amount of tissue adhering to the sheet at a given iteration is discernibly less than that adhering to the sheet used in the immediately preceding iteration. When this occurs, the exfoliation process is completed. The method described above promotes immediate, optimal and temporary cosmetic improvements while at the same time preventing excessive epidermal loss, which can lead to undesirable irritation.

The end points of the processes recited above are user-specific. Both the amount of tissue exfoliated in each of the first few iterations, and the optical density at which a visually discernible drop off in density of removed tissue on the sheet is observed have been found to vary widely from individual to individual. However, for any given individual the visually discernible drop off in optical density has been found to occur at about the same optical density on each of his or her uses of the process. Hence, it is possible for an individual to select a particular optical density, representative of a respective amount of tissue on the exfoliation sheet, and to use that to set his or her end point for subsequent uses.

After the user has determined an end point that is satisfactory for his or her use of the exfoliation process, he or she may compare the sheet 10 that was removed at the end point of the process with a comparison sheet 28 that preferably has a plurality of discrete, visually distinct regions 29 representative of varying amounts of exfoliated tissue using the same type of film (e.g., reflective or transparent) that is being used for the exfoliation in question. The user can select, as a target for subsequent exfoliations, that one of the patterned regions on the comparison sheet that most closely visually matches the exfoliation sheet that he or she removed at his or her end point—i.e., that matches the optical density of exfoliated tissue at the point at which the amount of tissue exfoliated in each repetition of the process begins to fall off. The next time the user chooses to use the iterative exfoliation process of the invention, the end point can be obtained by visually matching each used exfoliation sheet 10 with a chosen target region 29 on a comparison strip until a close match occurs. This matching process is believed to be simpler, easier, and more precise than the initial process of comparing amounts of exfoliated tissues on sequential ones of a series of freshly removed sheets.

The visually distinct regions 29 on the comparison strip 28 may comprise printed indicia (e.g., as made by a silk screening operation), or may be embossed or otherwise formed on a transparent or reflective substrate preferably selected to have an appearance similar to that of the exfoliation sheet. The comparison strip 28 may be prepared from images of a series of used exfoliation sheets, where each of the images shows a differing amount of exfoliated tissue, and where each of the images is preferably selected from a portion of the respective sheet having no extraneous structural detail such as wrinkles, skin blemishes, etc. That is, each of the images is selected to represent a different visually discernible density of removed tissue. The sequence of images may then be reproduced on a transparent or reflective substrate by known means, such as embossing or screen printing, so as to form a sequence of patterned regions 29 running from a densest to a least dense region. Although the drawing depicts a single, separate comparison strip 28 supplied as a portion of an exfoliation kit 30, it will be understood by those skilled in the art that one could choose to supply an array of patterned regions 29 as an edge portion of each exfoliation sheet. For example, one could screen a pattern of indicia onto a strip running along the edge of each sheet before coating the sheet with adhesive. In this arrangement, one would preferably leave the comparison portion of the sheet free of adhesive so as to avoid exfoliating skin onto the comparison portion, which would degrade the visual quality of the pattern of indicia during exfoliation.

The exfoliation methods taught herein are believed to be much less likely to cause irritation than are approaches using exfoliant chemicals. In following the processes of the invention the user will note that the tenacity of adhesion of sequential ones of the sheets will begin to slowly fall off at about the same time that the user's tactile sensitivity to the exfoliation process begins to slowly increase with further, and sometimes unnecessary, exfoliation steps. Both the onset of minor irritation and the loss of tenacity occur when substantially all of the dry, dead portion of the epidermis has been removed and a moist epidermal layer is revealed. Thus, various methods of the invention comprise at least three different discernible end points: visible reduction in size of a blemish; a visible decrease in the exfoliated amount of tissue on a film; and a noticeable decrease in tenacity of the adhesive to the skin.

The exfoliation processes described above have been found to be more effective when a parting angle (denoted with the Greek letter $\alpha$ (in FIG. 1) is maximized by pulling the initially detached edge 18 of the sheet along that portion of the body still covered with the balance of the sheet. That is, the amount of exfoliated tissue 15 is increased by removing the sheet 10 while holding the detached edge 18 in contact with, or as close as possible to, the adhesive-free surface 19 of the sheet 10. Removing the sheet 10 at a more acute parting angle (e.g., by pulling perpendicular to the body instead of pulling along the sheet-covered portion) results in the exfoliation of less tissue. It may be noted that the sheet 10 is depicted in FIG. 1 as being unrealistically thick so that various portions of the sheet can be more clearly pointed out. The preferred approach thus reduces both the number of sheets used and the number of times a user must apply sheets.

As noted above, inspection of the exfoliation sheet or film to determine a process end point by monitoring the amount of material removed may be carried out on exfoliating films having a high degree of transparency, as well as on those having a reflecting surface. Thus, the end point can be determined by inspecting the used exfoliation sheets in either transmitted or reflected light.

An initially preferred exfoliation sheet 10 comprised a piece of a pressure-sensitive transparent tape of the sort commonly used for sealing packages to be shipped by the postal service or by another common carrier. Many sorts of pressure-sensitive transparent tapes were initially used to practice the invention. A preferred material, comprising a pressure sensitive hot melt rubber resin on a biaxially oriented polypropylene film base, is sold by the Masking and Packaging Systems Division of the 3M Corporation as Scotch Brand Type 375 Box Sealing Tape. This tape has an adhesion to steel of fifty five ounces per inch of tape width, as measured by ASTM Test D-3330. Another polypropylene film tape, having a pressure sensitive adhesive, that was initially used successfully, is a similar product having a somewhat lower adhesion to steel. This product is sold by the 3M Corporation as their Highland Brand Type 3565 Utility Label Protection Tape.

A presently preferred exfoliation sheet 10 is made from films of the type sold by the 3M Corporation under the trade name "Radiant Light Films". This category of films includes at least products cataloged as Type CM500, Type CM590 and Type VM2000 films, all of which use a reflective layer 60 comprising multiple thin polymer films of controlled thickness and index of refraction that are sandwiched between transparent exterior layers. This approach provides a non-metallic sheet having a high specular reflectance. Exfoliation sheets are made from these films by coating them with a transparent pressure-sensitive adhesive that is preferably selected from adhesives known to be of medical grade quality and hypo-allergenic. An advantage of these and other specularly reflective films is that the user can view a used exfoliation sheet in specularly reflected light, rather than in transmitted light. Moreover, because the specularly reflected light used in the examination passes through the exfoliated tissue twice, rather than once as is the case when viewing in transmission, the results of an exfoliation step are more clearly illuminated on the film and show more of the translucent skin material that has been removed. The preferred sheets also transmit light, so at least the Type CM500 and Type CM590 materials can also be examined in transmitted light if the user so chooses.

Handling a relatively large flexible adhesive-coated sheet can be problematic and can lead to wastage if two portions of the adhesive-coated surface come into contact with each other, causing adhesive-to-adhesive binding, which effectively destroys the sheet. One approach to overcoming this difficulty is to use a rigid rod 26 attached to that edge of the sheet 10 that is to be removed first. Another approach is to remove a backing sheet 22 from only a portion of the exfoliation sheet 10 and to then hold and manipulate the sheet by using the remaining portion of the backing sheet.

An exfoliation kit 30 can be prepared by adhering one or more easily removed backing sheets 22, to each of a plurality of pre-cut sheets. For example, for exfoliating a person's facial region, one can use a large sheet having a length 50 substantially equal to an ear-to-ear distance measured along a horizontal contour on a human head and a width 52 substantially equal to twice a vertical distance measured from a chin to an eye on the human head. In one such case a sheet of this sort has dimensions of about twelve by nine inches. In a preferred embodiment a backing sheet 22 is die-cut along an outline 54 representative of a cylindrical wrapping of the human face by well known cutting means that cut through the backing sheet 22 without cutting the underlying exfoliation sheet 10, so that a portion 22a of the backing sheet can be removed so as to expose a corresponding portion of the adhesive layer 12. Additionally, alignment indicia 56 representative of anatomical features, such as facial features, may be imprinted on the exfoliation sheet 10 to indicate to a user how to align the sheet with his or her face. Such indicia may be imprinted on either or both of an exfoliation sheet and a backing sheet as long as the printing is visible when the exfoliation sheet is ready to be used. In a preferred embodiment the alignment indicia may comprise a medial nose line 56a and/or eye indications 56b imprinted on the exfoliation sheet.

Figure 4:
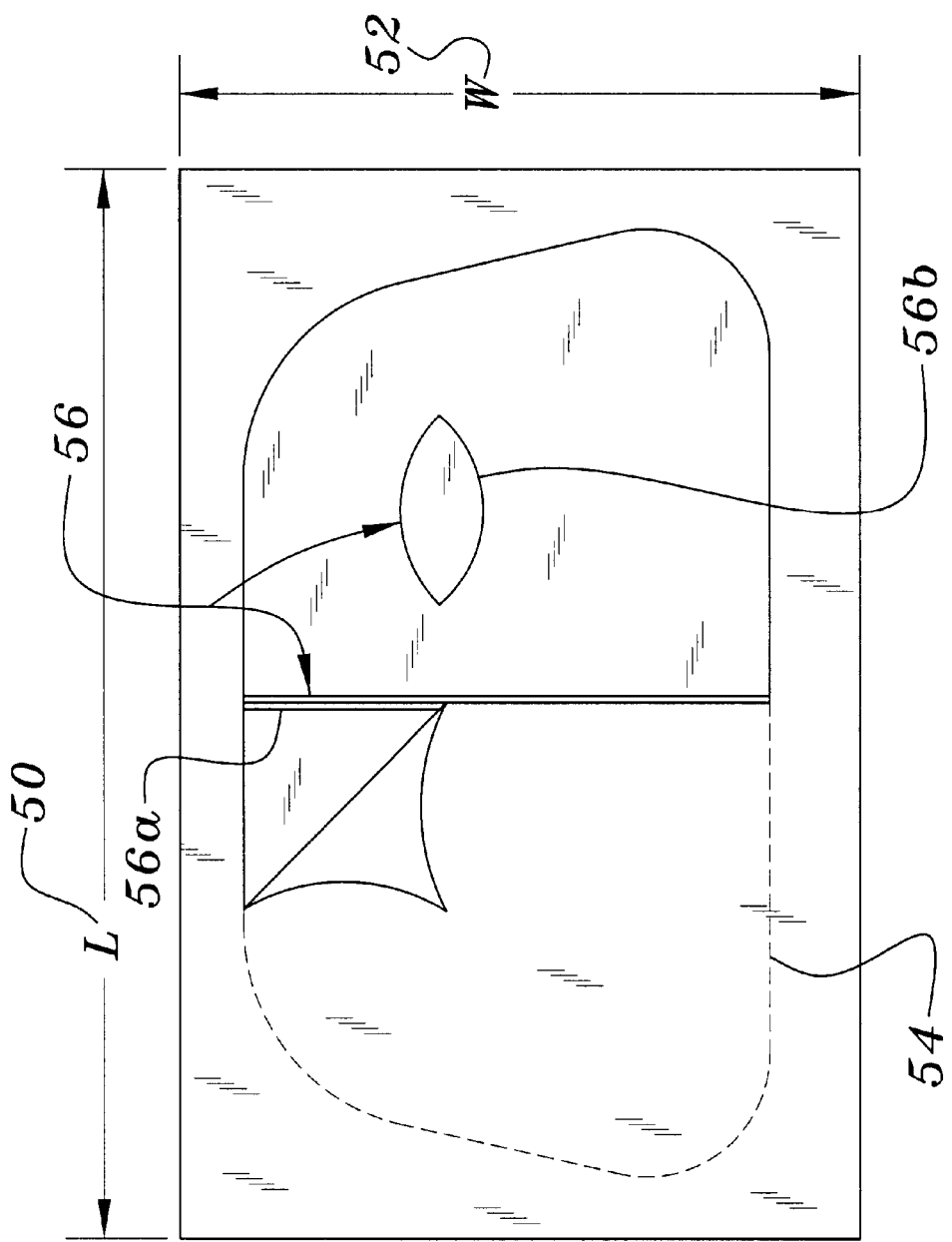
FIG. 4 is elevational view of a backing sheet partially removed from a portion of an exfoliation sheet having alignment indicia imprinted thereon.

In carrying out a preferred method of facial skin exfoliation using the kit 30, a user may select one of the pre-cut composite sheets 20 from the kit 30 and remove that portion of the backing sheet 22 overlying the active portion of the adhesive 12, as depicted in FIG. 4. The user then grasps the sheet at one or more of those portions still covered by the backing sheet, places the medial nasal indicium 56a along the vertical mid-line of his or her face, and gently rubs the adhesive-free side 32 of the exfoliation sheet 20 from the midline of his or her face toward one of the lateral margins thereof. After the sheet 12 is well adhered to the face, the user pulls the free end from the lateral margin of the face while holding the free edge as close to the adhesive free surface 32 as is practical—i.e., the sheet is pulled so that the lateral margin of it is immediately adjacent the face. After removing the sheet, the user can visually examine it to determine the amount of tissue exfoliated from various specific regions of his or her face, as indicated by the imprinted alignment indicia. More generally, the exfoliation sheet may have one or more indicia disposed on it, each of the one or more indicia representative of an anatomical feature of a selected portion of a user's body. Each of the one or more indicia is aligned with the respective anatomical feature when the exfoliation sheet is adhered to the body. Subsequent to removal of the exfoliation sheet, the alignment indicia can serve to show the user the relative amount of tissue exfoliated from various regions of the selected portion of the body.

In exfoliating the skin on a person's face, it is convenient to use a single complete sheet large enough to extend from the chin to the hairline in one direction and from the midline of the face at the bridge of the nose to the inner edge of the ear in a transverse direction. It is also convenient to use a sheet that is approximately twice that long—i.e., one that extends from ear to ear along a horizontal contour of a person's head. Moreover, when using the large convenient sheets, one can arrange to have a backing sheet die cut to be removable as a single piece from the active area, or may have it cut so as to be removable separately from the left and right side of the exfoliation sheet, or may choose to have smaller cut-outs arrayed across the sheet. This use of a large sheet allows the user to maximize the area being exfoliated while allowing continued and uninterrupted vision and respiration during the process. In using a large exfoliation sheet of this sort, a preferred exfoliation method calls for rubbing a small amount of a lubricant, such as petroleum jelly or other lubricant, onto the eyelids, eyebrows and other hair-covered portions of the body that may come in contact with the adhesive-coated surface of the exfoliation sheet. Thus, a preferred kit 30 may include a small tube of lubricant 36. It may be noted, however, that comfortable exfoliation operations have been frequently carried out without the use of lubricant. For example, accidental removal of eyebrow hair is rare because these hairs grow out at an angle closely matching the preferred parting angle.

An exfoliation kit 30 of the invention may, in a preferred embodiment, comprise a plurality of pre-cut composite sheets 20, which may have alignment indicia imprinted on them, a handle 24 selected to have substantially the same length as an edge of one of the sheets, a supply of lubricant or other masking material 36, a skin quantity comparison sheet 28 separate from or attached to ones of the sheets, and a suitable display package 38. The display package 38 may conveniently be a blister package comprising a cardboard back 40 and a transparent plastic blister overlay 42. It may be noted that the composite sheet may comprise a reflective exfoliation sheet having a transparent adhesive layer on both of its surfaces and having a respective backing sheet temporarily adhered to each surface. Because both sides of the preferred reflective sheet are equally mirror-like, an arrangement of this sort can economize on the use of relatively expensive reflective sheets.

Although the present invention has been described with respect to several preferred embodiments, many modifications and alterations can be made without departing from the invention. Accordingly, it is intended that all such modifications and alterations be considered as within the spirit and scope of the invention as defined in the attached claims.

What is claimed is:

1. A kit for exfoliating a portion of epidermis from a selected portion of a human body, the kit comprising, in combination:
    at least one flexible exfoliation sheet comprising a reflective surface, the sheet further comprising a transparent adhesive coating; and
    at least one comparison sheet displaying a plurality of visually distinct regions, each of the regions having a respective visual appearance representative of a predetermined amount of exfoliated skin.

2. The kit of claim 1 wherein the visually distinct regions are printed on the at least one comparison sheet.

3. the kit of claim 1 wherein each of the visually distinct regions is prepared from an image of a respective used exfoliation sheet.

4. The kit of claim 1 wherein the reflective surface comprises a specular layer comprising a plurality of thin polymer films.

5. A flexible sheet for exfoliating a portion of epidermis from a selected portion of a human body;

the flexible sheet comprising an adhesive layer for adhering the sheet to the selected portion of epidermis;

the flexible sheet further comprising at least one visible alignment indicium disposed thereon so as to be visible when the sheet is ready to be used, the indicium representative of at least one anatomical feature of the selected portion of the body.

6. The flexible sheet of claim 5 wherein the sheet comprises an exfoliation sheet having the adhesive layer coated on one surface thereof and wherein the at least one indicium is printed on the exfoliation sheet.

7. The flexible sheet of claim 5 wherein the sheet is a composite sheet comprising an exfoliation sheet and a backing sheet and wherein the alignment indicium is printed on a portion of the backing sheet that is not separated from the exfoliation sheet when the adhesive layer is ready to be adhered to the selected portion of the body.

8. The flexible sheet of claim 5 wherein the sheet has a specularly reflective surface and wherein the adhesive is transparent.

9. The flexible sheet of claim 5 wherein the selected portion of the body comprises a face and wherein one of the at least one indicium comprises a medial line representative of a nose.

10. A method of exfoliating a portion of epidermis from a selected portion of a human body, the method comprising the steps of:

providing a flexible sheet comprising an adhesive layer, the sheet having at least one alignment indicium representative of a respective anatomical feature printed thereon so as to be visible prior to the use of the sheet;

adhering the flexible sheet to the selected portion of the body, the flexible sheet adhered to the selected portion of the body so that each of the at least one indicium is aligned with the corresponding anatomical feature;

pulling the flexible sheet from the body and then viewing the relative amount of epidermis removed from at least two regions of the selected portion of the body as defined by the printed indicium.

11. The method of claim 10 wherein the step of determining the amount of epidermis removed from one of the regions is made by visually comparing the flexible sheet with a comparison sheet that displays a plurality of visually distinct regions, each of the regions having a respective visual appearance representative of a predetermined amount of exfoliated epidermis.

12. A method of exfoliating a portion of epidermis from a selected portion of a human body by using a flexible exfoliation sheet having a transparent adhesive layer disposed on at least one of two surfaces thereof, the sheet comprising a specularly reflective layer acting to reflect light incident on the adhesive layer, the method comprising the sequentially executed steps of:

a) adhering the flexible exfoliation sheet to the selected portion of the body by means of the adhesive;

b) removing the sheet from the selected portion of the body; and c) exposing the film to the light incident on the adhesive layer and viewing the removed material on the exfoliation sheet by means of the light reflected from the specularly reflective layer.

13. The method of claim 12 wherein the specularly reflective layer comprises a plurality of thin polymer films having respective selected thicknesses and respective selected indices of refraction, the thin films comprising a portion of the exfoliation sheet.

14. The method of claim 12 further comprising a step (d) after step (c) of:

d) repeating steps a) through c), using a different one of a plurality of the flexible exfoliation sheets for each repetition, until the amount of exfoliated tissue determined in one of the repeated steps c) is less than the amount of exfoliated tissue determined in the immediately previous repetition of step c).

15. The method of claim 12 further comprising a step (d) after step (c) of:

d) comparing the removed exfoliation sheet with a comparison sheet displaying a plurality of visually distinct regions, each of the regions having a respective visual appearance representative of a predetermined amount of exfoliated skin.

16. A method of exfoliating a portion of epidermis from a selected portion of a human body to produce an immediate improvement by reducing the visible size of a blemish disposed thereon, the method comprising the sequentially executed steps of:

a) separating a flexible exfoliation sheet having a surface coated with a pressure-sensitive adhesive from an adhesive-free surface of a supply of exfoliation material;

b) applying the pressure-sensitive adhesive-coated surface of the flexible exfoliation sheet to the selected portion of the body;

c) pulling the sheet from the selected portion of the body so as to remove the exfoliation sheet therefrom;

d) visually inspecting the predetermined portion of the body to see if the visible size of the blemish has been substantially reduced, and, if the visible size of the blemish has not been substantially reduced;

e) consecutively repeating steps a) through d) until observing, in one of the repetitions of step d), that the visible size of the blemish has been substantially reduced.

* * * * *

UNITED STATES PATENT AND TRADEMARK OFFICE
CERTIFICATE OF CORRECTION

PATENT NO.    : 6,563,012 B2
DATED         : May 13, 2003
INVENTOR(S)   : John M. Hill It is certified that error appears in the above-identified patent and that said Letters Patent is hereby corrected as shown below:

Column 8,
Line 57, insert -- pre-printed thereon -- after "visually distinct regions".
Line 62, replace "the kit" with -- The kit --.

Column 9,
Line 6, replace -- disposed -- with "pre-printed".
Line 33, replace -- printed -- with "pre-printed".

Column 10,
Line 41, insert -- at least a portion of -- after "applying".
Line 51, replace "repeating steps a) through d)" with
-- repeating at least steps b) through d) --.

Signed and Sealed this

Eighth Day of July, 2003

JAMES E. ROGAN
*Director of the United States Patent and Trademark Office*